United States Patent [19]  
Crast, Jr. et al.

[11] B  3,985,741  
[45] Oct. 12, 1976

[54] PRODUCTION OF p-HYDROXYCEPHALEXIN

[75] Inventors: Leonard Bruce Crast, Jr., Clay; William Joseph Gottstein, Fayetteville, both of N.Y.

[73] Assignee: Bristol-Myers Company, New York, N.Y.

[22] Filed: Oct. 18, 1974

[21] Appl. No.: 516,047

[44] Published under the second Trial Voluntary Protest Program on February 10, 1976 as document No. B 516,047.

Related U.S. Application Data

[62] Division of Ser. No. 289,703, Sept. 15, 1972, abandoned.

[52] U.S. Cl. .............................. 260/243 C; 424/246  
[51] Int. Cl.² ........................................ C07D 501/12  
[58] Field of Search ............................... 260/243 C

[56] References Cited  
UNITED STATES PATENTS  
3,708,478  1/1973  Chapman et al. ............... 260/243 C  
3,867,380  2/1975  Dunn et al. ..................... 260/243 C

*Primary Examiner*—Nicholas S. Rizzo  
*Attorney, Agent, or Firm*—Herbert W. Taylor, Jr.

[57] ABSTRACT

Improved yields of 7-[D-α-amino-α-(4-hydroxy- and 3-chloro-4-hydroxy-phenyl)acetamido]-3-methyl-3-cephem-4-carboxylic acids are obtained by acylating 7-aminodesacetoxycephalosporanic acid with the mixed anhydride (from ethyl chloroformate) of the ring-substituted 2-phenylglycine when the latter's α-amino group has been blocked by reaction with a β-keto compound such as methyl acetoacetate. Improved purification processes include the use of dimethylformamide and acetonitrile solvates and solvates and bis-anthraquinone-1,5-disulfonic acid salts.

2 Claims, No Drawings

PRODUCTION OF P-HYDROXYCEPHALEXIN

CROSS-REFERENCE TO RELATED APPLICATIONS

This application is a division of our prior copending application filed Sept. 15, 1972 as Ser. No. 289,703 and now abandoned.

BACKGROUND OF THE INVENTION

1. Field of the invention.

The two, previously disclosed cephalosporins of the present invention possess the usual attributes of such compounds and are particularly useful in the treatment of bacterial infections, especially by oral administration. This invention provides improved processes for their production, isolation and purification.

2. Description of the prior art

The literature on cephalosporins has been reviewed, for example, by E. P. Abraham, *Pharmacol. Rev.* 14, 473–500 (1962), by I. M. Rollo, *Ann. Rev. Pharmacol.* 6, 218–221 (1966), by E. P. Abraham, *Quart. Rev.* (London) 21, 231 (1967), by E. Van Heyningen, *Advan. Drug Res.*, 4, 1–70 (1967), by G. T. Stewart, *The Penicillin Group of Drugs*, Elsevier Publishing Company, New York, New York (1965) at pages 185–192 and briefly in *Annual Reports in Medicinal Chemistry*, Academic Press, Inc. 111 Fifth Avenue, New York, New York, 10003, by L. C. Cheney on pages 96–97 (1967), by K. Gerzon and R. B. Morin on pages 90–93 (1968), by K. Gerzon on pages 78–80 (1969) and by L. H. Conover on pages 101–102 (1970). New cephalosporins are frequently reported at the annual Interscience Conference on Antimicrobial Agents and Chemotherapy as illustrated by Sassiver et al., *Antimicrobial Agents and Chemotherapy*, , 1968, American Society for Microbiology, Bethesda, Maryland, pages 101–114 (1969) and by Nishida et al., ibid, 236–243 (1970). Two excellent recent reviews are The Cephalosporins Microbiological, Chemical and Pharmacological Properties and Use in Chemotherapy of Infection, L. Weinstein and K. Kaplan, *Annals of Internal Medicine*, 72, 729–739 (1970) and Structure Activity Relationships Among Semisynthetic Cephalosporins, M. L. Sassiver and A. Lewis, *Advances in Applied Microbiology*, edited by D. Perlman, 13, 163–236 (1970), Academic Press, New York.

The original syntheses of 7-[D-α-amino-α-(4-hydroxy- and 3-chloro-4-hydroxy-phenyl)acetamido]-3-methyl-3-cephem-4-carboxylic acid, which have the structure

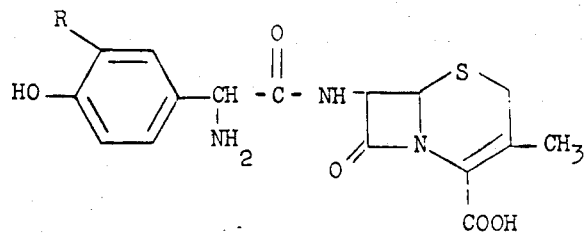

wherein R is hydrogen or chloro were disclosed in U.S. Pat. Nos. 3,489,751 and 3,489,752, both issued Jan. 13, 1970 (corresponding to Farmdoc No. 36,496, Netherlands Pat. No. 68/12382; Canada Pat. Nos. 842,799 and 842,800 and U.K. Pat. No. 1,240,687).

There are numerous patents and publications dealing with the simpler, related compound containing no substituents in the benzene ring which is the well-known antibacterial agent cephalexin. For example, syntheses of cephalexin are disclosed in Lilly's U.S. Pat. Nos. 3,507,861; 3,671,449; Belgium Pat. No. 737,761 (Farmdoc No. 12,621R; France Pat. No. 2,016,284) and U.K. Pat. No. 1,174,335 (Farmdoc No. 28,654) and Glaxo's West Germany Pat. No. 2,063,268 (Farmdoc No. 46,839S); Glaxo's U.S. Pat. Nos. 3,634,416 and 3,676,437 and Osaka's Japanese Pat. No. 72/24714R (Farmdoc No. 47,321S); *J. Med. Chem.*, 12, 310–313 (1969) and *J. Org. Chem.* 36(9), 1259–1267 (1971).

Various salts, hydrates and complexes of cephalexin and processes for isolating and purifying cephalexin are disclosed in some of the above and in Lilly's U.S. Pat. Nos. 3,502,663; 3,655,656; 3,531,481; 3,676,434 and Glaxo's Belgium Pat. No. 753,910 (Farmdoc No. 08214S) and Belgium Pat. No. 764,055 (Farmdoc No. 60,231S; Canada Pat. No. 881,195). See also *Journal of Pharmaceutical Sciences*, 59(12), 1809–1814 (1970).

Of this cephalexin art only U.S. Pat. Nos. 3,507,861; 3,671,449; 3,634,416 and U.K. Pat. No. 1,174,335 make any reference to substituents in cephalexin's benzene ring; such disclosure in these four references is completely general in nature and includes no physical constants, yields or the like. None of these general disclosures appear to contemplate any particular disubstitution in the benzene ring and certainly no such compound is named.

SUMMARY OF THE INVENTION

It was the object of the present invention to provide improved processes for the production, isolation and purification of the two 7-[D-α-amino- -(4-hydroxy- and 3-chloro-4-hydroxy phenyl)acetamido]-3-methyl-3-cephem-4-carboxylic acids. The phenolic hydroxyl group, for whatever reason, makes it very difficult to obtain high yields. Of the methods disclosed in U.S. Pat. Nos. 3,489,751 and 3,489,752 the highest yields obtained by us have been by the t-BOC method but they were not as high as is desired for commercial production and in addition the reagent used in the t-BOC process is very expensive.

These objectives have been attained by the provision, according to the present invention, of the process for producing a compound in the D configuration of the formula

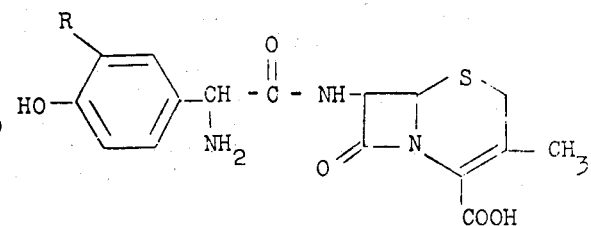

wherein R is hydrogen or chloro which comprises the consecutive steps of a. Acylating 7-aminodesacetoxycephalosporanic acid or a carboxylic acid salt thereof with an acid in the D configuration of the formula

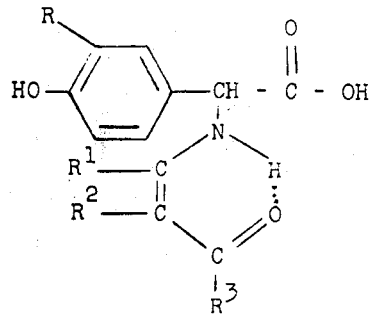

wherein R is hydrogen or chloro, $R^1$ is alkyl, aralkyl or aryl, $R^2$ is hydrogen, alkyl, aralkyl or aryl and $R^3$ is alkyl, aralkyl, aryl, alkoxy, aralkoxy, aryloxy or

wherein $R^4$ and $R^5$ are each hydrogen, alkyl, aralkyl or aryl or, when taken together with the nitrogen atom, are piperidino or morpholino, or an acylating derivative thereof in an inert solvent at a temperature below 0°C., and b. removing the α-amino-protecting group.

In this process it is preferred that there is also present during step (a) a compound of the formula

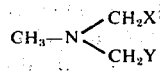

wherein X is a hydrogen atom or an alkyl or phenyl group, Y is a hydrogen atom or a lower alkyl group, or X and Y together represent any one of the divalent radicals, ethylene, substituted ethylene, trimethylene, $—CH_2OCH_2—$ or $—CH_2N(CH_3)CH_2—$. Examples of such catalysts are N-methylmorpholine and N,N-dimethylbenzylamine. It is preferred that the inert solvent be acetone or aqueous acetone and that the 7-ADCA be in the form of its triethylamine salt and the acylating derivative be also that a mixed anhydride formed from an alkyl chlorocarbonate.

It is further preferred that, in the amino-protecting group, $R^1$ is methyl, $R^2$ is hydrogen and $R^3$ is methoxy, ethoxy or methyl; this requires the use of methyl acetoacetate, ethyl acetoacetate or acetylacetone.

In the removal of the α-amino-protecting group it is preferred that use be made of a strong mineral acid such as hydrochloric acid or of formic acid.

The present invention also provides a process of purifying a crude form of the acid 7-[D-α-amino-α-(3-chloro-4-hydroxyphenyl)-acetamido]-3-methyl-3-cephem-4-carboxylic acid which comprises dissolving said crude acid in heated, acidic aqueous acetonitrile and then cooling the solution and raising the pH to precipitate substantially pure, crystalline 7-[D-α-amino-α-(3-chloro-4-hydroxyphenyl)-acetamido]-3-methyl-3-cephem-4-carboxylic acid. In this process it is preferred that the acidic pH is below 2 and is subsequently raised to 4–5 and that the pH is raised by the addition of a tertiary amine, preferably a tertiary alkylamine and especially triethylamine.

The present invention also provides a process of purifying a crude form of the acid 7-[D-α-amino-α-(3-chloro-4-hydroxyphenyl)-acetamido]-3-methyl-3-cephem-4-carboxylic acid which comprises converting said crude acid to its solid bis-anthraquinone-1,5-disulfonic acid salt, isolating said solid salt and then dissolving it, e.g. in aqueous acetonitrile, and adding a base e.g. to about pH 5 to precipitate spontaneously substantially pure, crystalline 7-[D-α-amino-α-(3-chloro-4-hydroxyphenyl)-acetamido]-3-methyl-3-cephem-4-carboxylic acid. Thus a preferred intermediate in this purification is substantially pure, crystalline 7-[D-(-)-α-amino-α-(3-chloro-4-hydroxyphenyl)acetamido]-3-methyl-3-cephem-4-carboxylic acid bis-anthraquinone-1,5-disulfonate.

The present invention also provides a process of purifying a crude form of the acid 7-[D-α-amino-α-(4-hydroxyphenyl)-acetamido]-3-methyl-3-cephem-4-carboxylic acid which comprises converting said crude acid to its solid bis-anthraquinone-1,5-disulfonic acid salt, isolating said solid salt and then dissolving it, e.g. in aqueous acetonitrile, and adding a base, e.g. to about pH 5 to precipitate spontaneously substantially pure, crystalline 7-[D-α-amino-α-(4-hydroxyphenyl)-acetamido]-3-methyl-3-cephem-4-carboxylic acid. Thus a preferred intermediate in this purification is substantially pure, crystalline 7-[D-(-)-α-amino-α-(4-hydroxyphenyl)-acetamido]-3-methyl-3-cephem-4-carboxylic acid bis-anthraquinone-1,5-disulfonate.

The present invention also provides a process of purifying a crude form of 7-[D-α-amino-4-hydroxyphenylacetamido]-3-cephem-4-carboxylic acid which comprises converting said crude acid to its solid, crystalline dimethylformamide solvate containing 1.5 moles dimethylformamide per mole of said acid, isolating said solid solvate, slurrying it in nearly boiling methanol, preferably at about 50°C., until the solvate dissociates, cooling the suspension and then collecting therefrom substantially pure, solid 7-[D-α-amino-4-hydroxyphenylacetamido]-3-cephem-4-carboxylic acid. Thus a preferred intermediate in this purification is the substantially pure, crystalline dimethylformamide solvate of 7-[D-α-amino-4-hydroxyphenylacetamido]-3-cephem-4-carboxylic acid containing 1.5 moles dimethylformamide per mole of said acid.

The present invention also provides a process of purifying a crude form of 7-(D-α-amino-3-chloro-4-hydroxyphenylacetamido)-3-cephem-4-carboxylic acid which comprises converting said crude acid to its solid, crystalline dimethylformamide solvate containing 1.5 moles dimethylformamide per mole of said acid, isolating said solid solvate, slurrying it in nearly boiling methanol, preferably at about 50°c., until the solvate dissociates, cooling the suspension and then collecting therefrom substantially pure, solid 7-[D-α-amino-3-chloro-4-hydroxyphenylacetamido]-3-cephem-4-carboxylic acid. Thus a preferred intermediate in this purification is the substantially pure, crystalline dimethylformamide solvate of 7-(D-α-amino-3-chloro-4-hydroxyphenylacetamido)-3-cephem-4-carboxylic acid containing 1.5 moles dimethylformamide per mole of said acid.

DETAILED DESCRIPTION

The acylating acid is preferably in the form of its mixed acid anhydride, but its functional equivalent as an acylating agent for a primary amine may also be utilized. Preferred mixed anhydrides include particularly the mixed anhydrides prepared from stronger acids such as the lower aliphatic monoesters of carbonic acid, of alkyl and aryl sulfonic acids and of more hindered acids such as diphenylacetic acid. In addition, an acid azide or an active ester or thioester (e.g., with p-nitrophenol, 2,4-dinitrophenol, thiophenol, thioacetic acid) may be used, or the free acid itself may be coupled with 7-aminodesacetoxycephalosporanic acid after first reacting said free acid with N,N'-dimethylchloroformiminium chloride [cf. Great Britain Pat. No. 1,008,170 and Novak and Weichet, Experientia XXI/6, 360 (1965)] or by the use of enzymes or of an N,N'-carbonyldiimidazole or an N,N'-carbonylditriazole [cf. South African Pat. No. 63/2684] of a carbodiimide reagent [especially N,N'-dicyclohexylcarbodiimide, N,N'-diisopropylcarbodiimide or N-cyclohexyl-N'-(2- morpholinoethyl)carbodiimide; cf. Sheehan and Hess, J. Amer. Chem. Soc. 77, 1067, (1955)], or of alkynylamine reagent [cf. R. Buijle and H. G. Viehe, Angew Chem. International Edition 3, 582 (1964)], or of a ketenimine reagent [cf. C. L. Stevens and M. E. Monk, J. Amer. Chem. Soc, 80, 4065, (1958)]or of an isoxazolium salt reagent [cf. R. B. Woodward, R. A. Olofson and H. Mayer, J. Amer. Chem. Soc. 83, 1010 (1961)]. Another equivalent of the acid chloride is a corresponding azolide, i.e. an amide of the corresponding acid whose amide nitrogen is a member of a quasiaromatic five-membered ring containing at least two nitrogen atoms, i.e. imidazole, pyrazole, the triazoles, benzimidazole, benzotriazole and their substituted derivatives. As an example of the general method for the preparation of an azolide, N,N′-carbonyldiimidazole is reaction with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield diimidazolides. The by-product, imidazole, precipitates and may be separated and the imidazolide isolated, but this is not essential. The methods for carrying out these reactions to produce a cephalosporin are well-known in the art (cf. U.S. Pat. Nos. 3,079,314; 3,117,126 and 3,129,224 and British Pat. Nos. 932,644; 957,570 and 959,054).

Examples of preferred acylating derivatives are mixed anhydrides (including those obtained by treating a salt of the acid in anhydrous medium preferably acetone, with an alkyl chlorocarbonate) and the intermediates formed by reaction with a carbodiimide, e.g. N,N′-dicyclohexylcarbodiimide, or with carbonyldimidazole.

In a preferred form of the invention the N-protected cephalosporins are not isolated but are hydrolyzed directly in situ.

The hydrolysis may be carried out in aqueous or partly aqueous solution, preferably between pH 1 and pH 5 and at ambient temperature.

In one method of carrying out the present invention the hydrolysis is effected by adding a small quantity of an aqueous solution of a mineral acid or strong organic acid (e.g. 90% formic acid) to a solution of an amine salt of the N-protected cephalosporin in an organic solvent or mixture of solvents.

An alternative method of carrying out the present invention is to treat an alkali metal salt of the N-protected cephalosporin with an aqueous acid solution, e.g. dilute acetic acid or very dilute hydrochloric acid.

The completion of hydrolysis is indicated by the disappearance of the starting N-protected cephalosporin, as shown by paper chromatography, the desired cephalosporin being isolated and purified by any one of the conventional procedures used for aminocephalosporins.

The starting acids in the form of their salts are conveniently prepared by condensing an α-amino acid or a salt thereof with a β-diketone or β-ketoester or β-ketoamide, methods of effecting such a condensation being described by Dane et al. (Angew Chem., 1962, 74, 873) and in U.S. Pat. No. 3,325,479.

Enhanced yields of the final cephalosporins can be obtained by the hydrolysis of solutions of the N-protected cephalosporins obtained by reacting 7-aminodesacetoxycephalosporanic acid (7-ADCA) or a salt thereof with a mixed anhydride prepared by a reaction involving the use of an alkali metal salt of the carboxylic acid in the presence of a small quantity of a catalyst.

The preferred catalysts have the general formula

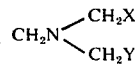

where X is a hydrogen atom or an alkyl or phenyl group, Y is a hydrogen atom or a lower alkyl group, or X and Y together represent any one of the divalent radicals, ethylene, substituted ethylene, trimethylene, —CH$_2$OCH$_2$— or —CH$_2$N(CH$_3$)CH$_2$—. Examples of such catalysts are N-methylmorpholine and N,N-dimethylbenzylamine.

Preferably the mixed anhydride is prepared in an inert water-miscible solvent, such as dry acetone, and is then allowed to react with an aqueous solution of a salt of 7-ADCA, e.g. an alkali metal salt or a salt with a tertiary amine such as triethylamine. After removal of the organic solvent the N-protected cephalosporin remains in the aqueous solution and is hydrolyzed directly to the free aminoacylcephalosporin by means of mineral acid. The liberated N-protecting agent is removed by solvent extraction, then the pH of the aqueous phase is raised so that the aminocephalosporin crystallizes.

The separation of the aminocephalosporin from the β-diketone or β-ketoester or β-ketoamide formed during the reaction may be effected by taking advantage of the solubility of such by-products in solvents, e.g. ether, chloroform or benzene, which do not dissolve the aminocephalosporin.

The following examples are given in illustration of, but not in limitation of, the processes and intermediates of the present invention. All temperatures are in degrees Centigrade. Although not important to the present invention it is to be understood that the two cephalosporins referred to herein as acids are actually zwitterions when solid; being amphoteric their ionic form in solution will vary with pH.

DESCRIPTION OF THE PREFERRED EMBODIMENTS

EXAMPLE 1

Sodium D-N-(2-methoxycarbonyl-1-methylvinyl)-α-amino-3-chloro-4-hydroxyphenylacetate Methyl acetoacetate (25.5 g., 0.22 mole) in methanol (200 ml.) was added to a stirred refluxing suspension of sodium D-(-)-α-amino-3-chloro-4-hydroxyphenyl-acetate in methanol (800 ml.), prepared by dissolving the sodium hydroxide (7.8 g., 0.195 mole) then adding 41.4 g. (0.2 mole) of the amino acid, all at room temperature (22°C.). A near solution resulted. After 40 min. reflux, the methanol was removed by distillation with the simultaneous addition of toluene, until the distillation temperature reached 100°C. After cooling in an ice bath for 1 to 20 hr., the product was collected by filtration, washed with toluene, air dried, then vacuum dried at 40°C. over P$_2$O$_5$ for 24 hours. The yield of sodium D-N-(2-methoxycarbonyl-1-methylvinyl)-α-amino-3-chloro-4-hydroxyphenylacetate was 60 g. (92%).

$[\alpha]_D^{22}$ degrees C. + 110°(c = 1%, H$_2$O)

Anal. Calcd. for $C_{13}H_{13}ClNO_5$. Na: C, 48.45; H, 4.07; N, 4.35; Cl, 11.02. Found: C, 48.24; H, 4.16; N, 4.53; Cl, 10.92.

7-[D-α-Amino-α-(3-chloro-4-hydroxyphenyl)-acetamido]-3-methyl-3-cephem-4-carboxylic acid To 450 ml. of dry acetone stirring at −10°C. was added 20 ml. (0.208 mole) of ethyl chloroformate followed by 12 ml. of 1% N-methylmorpholine in dry acetone followed by 64 g. (0.2 mole) of sodium D-N-(2-methoxycarbonyl-1-methylvinyl)-α-amino-3-chloro-4-hydroxyphenylacetate. The slurry was stirred at −10°C. for 20 min., then filtered, *directly* and *rapidly* through a pad of diatomaceous earth ("Dicalite"), into a rapidly stirred and previously prepared solution of 42.8 g. (0.2 mole) of 7-amino-3-cephem-3-methyl-4-carboxylic acid (7-ADCA) in 250 ml. of water, 250 ml. acetone and 30 ml. (0.217 mole) of triethylamine pre-cooled to −10°C. The temperature was kept at −10°C. for 10 min. then allowed to come to 0°C. over a 20 min. period. At this point, 6 N HCl was added dropwise to pH 6.4 and, after 15 min., the unreacted 7-ADCA was filtered off, washed with 100 ml. of 1:1 acetone-water, then acetone. The combined filtrates were then concentrated under reduced pressure at 22°C. to a volume of about 400 ml. (most of the acetone was removed). Next, with rapid stirring, a solution of 22 ml. of 90% formic acid in 500 ml. of methyl isobutyl ketone (MIBK) was added, all at once. The mixture was stirred in an ice bath for 1 hour. However, after about 15 min. a "gum ball" formed which required reduced stirring speed. After the hydrolysis, the MIBK layer was separated and discarded. To the aqueous and ppt. was added 500 ml. of acetonitrile and the mixture was heated slowly to 42°C. at which time a clear solution resulted. More acetonitrile was added to reach the cloud point at 42°C. and then the flask was scratched or seeded. After 30 min. at 42°C., the product was filtered off, washed with 80% acetonitrile-water (5:1), then acetonitrile and air dried. After vacuum drying over $P_2O_5$, the yield of 7-[D-α-amino-α-(3-chloro-4-hydroxyphenyl)-acetamido]-3-methyl13-cephem-4-carboxylic acid was 25 g. (30% of theory). Samples obtained in this manner were about 90% pure by NMR. They contained some starting acid and were solvated with acetonitrile, usually about ½ mole.

EXAMPLE 2

Purification of
7-[D-α-amino-α-(3-chloro-4-hydroxyphenyl)acetamido]-3-methyl-3-cephem-4-carboxylic acid A total of 180 g. of 7-[D-α-amino-α-(3-chloro-4-hydroxyphenyl)-acetamido]-3-methyl-3-cephem-4-carboxylic acid (average purity 90%) was dissolved in 500 ml. $H_2O$ and 500 ml. acetonitrile to which 6 N HCl was added dropwise witth stirring to pH 1.3. The solution was filtered and 1 liter of acetonitrile was added and the resulting solution heated to 42°C. while triethylamine was added to pH 4.5. The product crystallized rapidly and, after 30 min. at 42°C., was collected by filtration, washed with 80% acetonitrile-water, then acetonitrile and then air dried. The yield of purified 7-[D-α-amino-α-(3-chloro-4-hydroxyphenyl)acetamido]-3-methyl-3-cephem-4-carboxylic acid after vacuum drying at room temperature over $P_2O_5$, was 152 g.

A 1 g. sample was dried at 50°C. in vacuo with a stream of air bled into the oven to give an analytical sample; dec. pt. 200°C.

Anal. Calcd. for $C_{16}H_{16}ClN_3O_5S$: C, 48.24; H, 4.05; N, 10.56; Cl, 8.92. Found: C, 47.94; H, 4.38; N, 11.64; Cl, 8.08.

EXAMPLE 3

Purification of
7-[D-α-amino-α-(3-chloro-4-hydroxyphenyl)acetamido]-3-methyl-3-cephem-4-carboxylic acid One hundred fifty-one g. of 7-[D-α-amino-α-(3-chloro-4-hydroxyphenyl)-acetamido]-3-methyl-3-cephem-4-carboxylic acid was dissolved in 1500 ml. of water by the addition of 6 N HCl dropwise to pH 1.4. A small amount of ppt was filtered off. The pH was then adjusted to pH 4 with 20% NaOH and, again, a small amount of colored ppt was filtered off. Seeding or scratching with non-solvated crystals induced crystallization which was slow at first, then, after about 30 min., became rapid. After 1 hr. at 22° C. and 30 min. at 5°–10° C, the product was filtered off, washed well with water (3 × 200 ml.), then air dried and vacuum dried over $P_2O_5$ to constant weight. Yield 117 g. of purified 7-[D-α-amino-α-(3-chloro-4-hydroxyphenyl)acetamido]-3-methyl-3-cephem-4-carboxylic acid.

$[\alpha]_D^{24.5}$ + 164.1° (c = 1%, 0.1N HCl)

Anal. Calcd. for $c_{16}H_{16}ClN_3O_5S$: C, 48.24; H, 4.05; N, 10.56; Cl, 8.92. Found: C, 47.77; H, 4.10; N, 10.44; Cl, 8.43.

KF $H_2O$ 1.54%.

dec pt 222° C.

EXAMPLE 4

Bis-anthraquinone-1,5-disulfonic acid salt of 7-[D-α-amino-α-(3-chloro-4-hydroxyphenyl)acetamido]-3-methyl-3-cephem-4-carboxylic acid Nine g. of 60–80% pure 7-[D-α-amino-α-(3-chloro-4-hydroxyphenyl)acetamido]-3-methyl-3-cephem-4-carboxylic acid (contaminated with starting acid) was dissolved in water (100 ml.) by adding 6 N HCl to pH 2. Next, 8.24 g. (0.02 mole) of disodium anthraquinone-1,5-disulfonic acid was added and, after 1 hr. stirring at pH 2, the crude bis-anthraquinone-1,5-disulfonic acid salt of 7-[D-α-amino-α-(3-chloro-4-hydroxyphenyl)acetamido]-3-methyl-3-cephem-4-carboxylic acid was collected by filtration and recrystallized from hot water to give 6 g. of bis-salt.

Anal. Calcd. for $C_{46}H_{40}Cl_2N_6O_{18}S_4$. $H_2O$: C, 46.73; H, 3.49; S, 10.85; KF $H_2O$, 1.5; N, 7.11. Found: C, 46.11; H, 3.86; S, 10.75; KF $H_2O$, 3.23; N, 6.81.

The 6 g. of bis-anthraquinone-1,5-disulfonic acid salt of 7-[D-α-amino-α-(3-chloro-4-hydroxyphenyl)acetamido]-3-methyl-3-cephem-4-carboxylic acid was suspended in 50 ml. $H_2O$ and 20 ml. of acetonitrile and, with stirring, the pH was adjusted to 5 with 20% NaOH. The solution was filtered and scratched. There was obtained 3.45 g. of excellent quality 7-[D-α-amino-α-(3-chloro-4-hydroxyphenyl)acetamido]-3-methyl-3-cephem-4-carboxylic acid as an acetonitrile solvate containing about one mole of acetonitrile which is removed by drying.

$[\alpha]_D^{25}$ + 157°(c = 0.25%, 0.1N HCl)

EXAMPLE 5

Sodium D-N-(2-methoxycarbonyl-1-methylvinyl)-α-amino-α-(4-hydroxyphenyl)acetate To a stirred solution of 3.02 g. (0.078 mole) of NaOH in 320 ml. of methanol was added 13.4 g. (0.08 mole) of D-(-)-2-(p-hydroxyphenyl)glycine and the resulting mixture was heated at reflux while a solution of 9.6 ml. (0.088 mole) of methyl acetoacetate in 80 ml. of methanol was added over a thirty minute period. After an additional 30 min. refluxing, the methanol was distilled off while toluene was added at the same rate so as to keep approximately the same internal volume. When the internal temperature reached 100° C. the suspension was cooled in ice water for 4 hours, filtered, washed well with toluene, air dried, and vacuum dried over $P_2O_5$ to constant weight. Yield: 19 g. of sodium D-N-(2-methoxycarbonyl-1-methylvinyl)-α-amino-α-(4-hydroxyphenyl)acetate.

Anal. Calcd. for $C_{13}H_{14}NO_5Na$: C, 54.35; H, 4.92; N, 4.88. Found: C, 53.98; H, 5.18; N, 4.90.

7-[D-α-Amino-α-(4-hydroxyphenyl)-acetamido]-3-methyl-3-cephem-4-carboxylic acid A. To 225 ml. of dry acetone, stirred at −10° C., was added 11 ml. of ethyl chloroformate followed by 6 ml. of 1% N-methylmorpholine in acetone, followed by 28.7 g. (0.1 mole) of sodium D-N-(2-methoxycarbonyl-1-methylvinyl)-α-amino-α-(4-hydroxyphenyl)-acetate and the slurry stirred at −10° C. for 20 min. The slurry was then filtered rapidly through a 7 cm. Buchner funnel with a ⅛ inch diatomaceous earth ("Celite") pre-washed pad with suction into a violently stirred solution of 21.4 g. (0.1 mole) of 7-ADCA in 62.5 ml. $H_2O$, 125 ml. acetone and 14 ml. (0.1 mole) of triethylamine precooled to −10° C. After stirring 30 min. at −10° C. the pH was adjusted to 6.4 with 6 N HCl and after 15 min. the unreacted 7-ADCA was filtered off, washed well with acetone and the combined filtrates stirred (total volume 600 ml.) in an ice bath (5° C.) while 7 ml. of 90% formic acid was added, all at once. After about one hour the product began to crystallize and after two hours 75 ml. of ether was added dropwise over a two hour period and after stirring overnight (∼ 14 hours) the product was filtered off, washed well with 90% acetone-water then acetone and air dried. After vacuum drying over $P_2O_5$ overnight there was obtained 14g. of 7-[D-α-amino-α-(4-hydroxyphenyl)acetamido]-3-methyl-3-cephem-4-carboxylic acid.

B. Sixty grams of 7-[D-α-amino-α-(4-hydroxyphenyl)-acetamido]-3-methyl-3-cephem-4-carboxylic acid were dissolved by warming in 800 ml. of 95% methanol-$H_2O$ (∼50° C.), filtering and scratching to induce crystallization. After standing about 20 hours at 10°C. (cold room) there was collected 31 g. of material which was obtained after vacuum drying over $P_2O_5$ for 24 hours. This material is an unstable methanol solvate which is no longer completely crystalline after drying. Dec. pt. 210° C; $[\alpha]_D^{22}$ + 157° (C=1%, $H_2O$).

Anal. Calcd. for $C_{16}H_{17}N_3O_5S.1\ 1/2\ H_2O$; C, 49.23; H, 5.17; N, 10.77; $H_2O$, 6.9. Found: C, 48.45; H, 4.97; N, 10.61; $H_2O$, 7.44.

EXAMPLE 6

Purification of 7-[D-α-amino-α-(4-hydroxyphenyl)-acetamido]-3-methyl-3-cephem-4-carboxylic acid

A.

7-(D-α-amino-4-hydroxyphenylacetammido)-3-cephem-4-carboxylic acid dimethylformamide solvate To a solution of 11 ml. (0.1 mole) of ethyl chloroformate and 6 ml. of 1% N-methylmorpholine and 2 drops of dimethylformamide in 225 ml of acetone at −10° was added 28.7 g. (0.1 mole) of sodium D-α-(2-methoxycarbonyl-1-propen-2-ylamino)-4-hydroxyphenylacetate. The mixture was stirred for 20 min. and added to a solution of 21.4 g. (0.1 mole) of 7-amino-3-desacetoxycephalosporanic acid (7-ADCA) in 15.5 ml. of triethylamine, 65 ml. of water and 125 ml. of acetone cooled to −10°. The mixture was filtered through a ½ inch pad of diatomaceous earth ("Dicalite") with suction during the addition to remove any sodium chloride. The solution was stirred for 90 minutes and then warmed to 0° and the pH was adjusted with conc. hydrochloric acid to pH 6.4. The mixture was filtered and 5 g. of starting 7-ADCA was recovered. The volume was adjusted to 600 ml. with acetone and 7 ml. of 90% formic acid was added; after stirring at room temperature for 2 hr. 7-[D-α-amino-α-(4-hydroxyphenyl)-acetamido]-3-methyl-3-cephem-4-carboxylic acid precipitated as a hygroscopic solid and was collected by filtration and dissolved in 200 ml. of dimethylformamide, cooled for 1 hr. and crystalline 7-(D-α-amino-4-hydroxyphenylacetamido)-3-cephem-4-carboxylic acid dimethylformamide solvate precipitated and was collected to yield after air drying 7 g.;m.p. >150° slow decomp.

To obtain a second crop of 7-(D-α-amino-4-hydroxyphenylacetamido)-3-cephem-4-carboxylic acid dimethylformamide solvate the above acetone filtrate was evaporated on the flash evaporator to about 75 ml. at 40° (15 mm/Hg) and diluted with 500 ml. of acetone which precipitated a gummy solid. The acetone was decanted and the gummy solid was dissolved in 150 ml. of dimethylformamide (DMF) and stirred overnight to yield a crystalline solid which was collected, washed with 300 ml. of DMF and finally with acetone to yield after air drying 14 g. of crystalline 7-[D-α-amino-α-(4-hydroxyphenyl)acetamido]-3-methyl-3-cephem-4-carboxylic acid solvated with 1.5 moles of dimethylformamide.

Anal. Calcd. for $C_{16}H_{17}N_3O_5S.\ 1\ 1/2\ C_3H_7NO$. C, 52.05; H, 5.86; N, 13.32. Found: C, 51.60; H, 5.94; N, 13.03. Corrected for 3.15% water found by Karl Fischer.

$[\alpha]_D^{28}$ + 96° (water, C, 0.121).

IR: (KBr) 2600–3600 (NH, $NH_3^+$, OH); 1755 (β-lactam);

1700 (HN—C=O); 1655 ($(CH_3)_2NC=O$);

1600 ($CO_2^-$)$cm^{-1}$.

NMR: ($D_2O$+DCl) (ppm δ7.95 ( S, 1.5, O=C—H); 6.8–7.6 (m, 4 $C_6H_4$—); 5.63 (d, 1, $C_7$—H), 5.15 (s, 1, CHC=O); 5.03 (d, 1, $C_6$—H), 2.7–3.7 (m, 2, S—$CH_2$—≺, 3.02 + 2.85 (s,s, 4.5, 4.5 $(CH_3)_2N$), 1.87 (s, 3, ≻—$CH_3$)

B. Conversion of the dimethylformamide solvate to D-7-(α-amino-4hydroxyphenylacetamido)-3-cephem-4-carboxylic acid A mixture of 37 g. of the above solvate was slurried in 180 ml. of 90% methanol at 50° for 1½ hour. After cooling to 10° C. substantially pure, crystalline 7-[D-α-amino-α-(4-hydroxyphenyl)-acetamido]-3-methyl-3-cephem-4-carboxylic acid was collected to yield 21 g. (73%) m.p. 150° slow decomposition.

Anal. Calcd for $C_{16}H_{17}N_3O_5S$: C, 52.88; H, 4.71; N, 11.57; Found: C, 52.91; H, 4.98; N, 11.64; Karl Fischer 6.07; $[\alpha]_D^{28}$ +158° (C, 0.09 water), ir (KBr) 2600–3600 (NH, $NH_3^+OH$), 1760 (C— O), 1560 –1600 ($CO_2 \theta$) cm$^{-1}$.; nmr ($D_2O$, DCl) (ppm δ) 6.8 – 7.6 (m, 4—$C_6H_4$), 5.66 (d, 1, $C_7$—H)

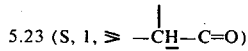

5.23 (S, 1, ≥ —CH—C=O)

5.07 (d, 1, $C_6$—H), 2.9–3.8 (m, 2, S—$CH_2$- ≤ 2.08 (S, 3, $CH_3$—C=).

EXAMPLE 7

Bis-Salt of p-hydroxycephalexin with anthraquinone-1,5-disulfonic acid

Approximately equivalent weights of p-hydroxycephalexin and anthraquinone-1,5-disulfonic acid disodium salt were combined in water plus dilute hydrochloric acid. The bis-salt, which crystallized at once, was collected by filtration, washed with water and air dried. The IR (KBr) spectrum was consistant and had the following characteristic absorptions: 1760 (broad, β-lactam), 1685 (broad, strong,amide COOH, quinone), near 1200 (broad) and 1040 cm$^{-1}$ (sulfonate).

P-Hydroxycephalexin is also named 7-[D-α-amino-α-(4-hydroxyphenyl)acetamido]-3-methyl-3-cephem-4-carboxylic acid.

We claim:

1. The process of purifying a crude form of 7-(D-α-amino-4-hydroxyphenylacetamido)-3-cephem-4-carboxylic acid which comprises converting said crude acid to its solid, crystalline dimethylformamide solvate containing 1.5 moles dimethylformamide per mole of said acid, isolating said solid solvate, slurrying it in nearly boiling methanol, preferably at about 50° C., until the solvate dissociates, cooling the suspension and then collecting therefrom substantially pure, solid 7-(D-α-amino-4hydroxyphenylacetamido)-3-cephem-4-carboxylic acid.

2. Substantially pure, crystalline dimethylformamide solvate of 7-(D-α-amino-4-hydroxyphenylacetamido)-3-cephem-4-carboxylic acid containing 1.5 moles dimethylformamide per mole of said acid.

* * * * *

UNITED STATES PATENT AND TRADEMARK OFFICE
CERTIFICATE OF CORRECTION

PATENT NO. : 3,985,741
DATED : October 12, 1976
INVENTOR(S) : Leonard B. Crast Jr. and William J. Gottstein It is certified that error appears in the above—identified patent and that said Letters Patent is hereby corrected as shown below:

In column 12 amend line 14 to read as follows:
"amino-4-hydroxyphenylacetamido)-3-methyl-3-cephem-4-car-".

In column 12, line 26, change "7-(D-α-amino-4-hydroxyphenylacetamido)-" to read: "7-(D-α-amino-4-hydroxyphenylacetamido)-3-methyl-".

Signed and Sealed this

Second Day of March 1982

[SEAL]

Attest:

GERALD J. MOSSINGHOFF

Attesting Officer     Commissioner of Patents and Trademarks